United States Patent [19]

Giacin et al.

[11] Patent Number: 5,455,023
[45] Date of Patent: Oct. 3, 1995

[54] LIQUID MOUTHWASH CONTAINING A PARTICULATE BICARBONATE SUSPENSION

[75] Inventors: Kenneth J. Giacin, Pennington; Amy L. Joseph, Hopewell, both of N.J.

[73] Assignee: Church & Dwight Co., Inc., Princeton, N.J.

[21] Appl. No.: 219,936

[22] Filed: Mar. 30, 1994

Related U.S. Application Data

[62] Division of Ser. No. 113,812, Aug. 31, 1993, Pat. No. 5,330,749, which is a division of Ser. No. 75,216, Jun. 10, 1993, Pat. No. 5,302,373.

[51] Int. Cl.⁶ .............................. A61K 7/16; A61K 9/10; A61K 33/30
[52] U.S. Cl. .............................. 424/49; 424/641; 424/642; 424/643; 424/717
[58] Field of Search .......................... 424/49–58

[56] References Cited

U.S. PATENT DOCUMENTS

| | | | |
|---|---|---|---|
| 3,954,962 | 5/1976 | Prussin | 424/49 |
| 4,132,770 | 1/1979 | Barth | 424/49 |
| 4,312,889 | 1/1982 | Melsheimer | 426/86 |
| 4,534,962 | 8/1985 | Marschner | 424/65 |
| 4,664,909 | 5/1987 | Marschner | 424/65 |
| 4,897,258 | 1/1990 | Rudy et al. | 424/53 |
| 5,043,183 | 8/1991 | Gershon et al. | 424/52 |
| 5,077,051 | 12/1991 | Gallopo et al. | 424/435 |
| 5,145,664 | 9/1992 | Thompson | 424/49 |
| 5,302,373 | 4/1994 | Giacin et al. | 424/49 |
| 5,330,749 | 7/1994 | Giacin et al. | 424/49 |

FOREIGN PATENT DOCUMENTS

| | | |
|---|---|---|
| 506563 | 9/1992 | European Pat. Off. |
| 94/04648 | 3/1994 | WIPO |
| 94/08558 | 4/1994 | WIPO |
| 94/07748 | 4/1994 | WIPO |
| 94/14407 | 7/1994 | WIPO |
| 94/14406 | 7/1994 | WIPO |

*Primary Examiner*—Shep K. Rose
*Attorney, Agent, or Firm*—Charles B. Barris

[57] ABSTRACT

This invention provides a mouthwash composition which is in the form of a concentrated aqueous ethanolic formulation of ingredients. An essential aspect of an invention mouthwash is an alkali metal bicarbonate ingredient which is present as a suspension phase of ultrafine particles. The suspension phase also can have a content of colloidal zinc oxide. Oral hygiene is practiced by diluting an invention mouthwash concentrate with water, and rinsing the oral cavity with the diluted liquid medium.

2 Claims, No Drawings

LIQUID MOUTHWASH CONTAINING A PARTICULATE BICARBONATE SUSPENSION

CROSS-REFERENCE TO RELATED APPLICATIONS

The present patent application is a divisional filing of patent application Ser. No. 08/113,812, filed Aug. 31, 1993, now U.S. Pat. No. 5,330,749; which in turn is a divisional filing of patent application Ser. No. 08/075,216, filed Jun. 10, 1993, now U.S. Pat. No. 5,302,373.

BACKGROUND OF THE INVENTION

Mouthwash compositions are liquid preparations which are formulated to cleanse and refresh the oral cavity.

Cosmetic mouthwashes usually contain water, alcohol, flavor and color ingredients, and have excellent consumer acceptance because the rinse medium has a refreshing mouthfeel, and the residual mouthwash ingredients have a pleasant aftertaste.

A wide variety of mouthwashes are available which contain various combinations of beneficial ingredients such as astringents, deodorants, antibacterial agents, healing agents, analgesics, buffers, humectants, surfactants, flavorants, preservatives, and the like.

It is desirable to include sodium bicarbonate as an ingredient in a mouthwash formulation because it provides deodorizing and buffering activities, and it contributes a clean mouthfeel and refreshing aftertaste in the oral cavity.

However, the effective inclusion of an alkali metal bicarbonate ingredient in a mouthwash has been limited by practical considerations. An alkali metal bicarbonate compound has a low level of solubility in an aqueous alcoholic solvent medium, so that any content of alkali metal bicarbonate in a typical mouthwash formulation is limited to less than about 2 weight percent. Further, a liquid mouthwash formulation containing a dissolved content of alkali metal bicarbonate does not have long term storage stability. The alkali metal bicarbonate ingredient in an aqueous alcoholic mouthwash formulation tends to discompose to alkali metal carbonate and carbon dioxide under storage conditions. Alkali metal carbonate has an irritating effect on the surfaces of an oral cavity.

Accordingly, it is an object of this invention to provide a liquid mouthwash formulation which contains up to 20 weight percent and higher of alkali metal bicarbonate ingredient.

It is another object of this invention to provide a liquid mouthwash formulation which contains a particulate suspension of alkali metal bicarbonate ingredient, and which exhibits superior dimensional stability under long term storage conditions.

Other objects and advantages of the present invention shall become apparent from the accompanying description and examples.

Of special background interest with respect to the present invention are publications which describe mouthwash and other dentifrice formulations containing alkali metal bicarbonate, such as U.S. Pat. Nos. 4,370,314; 4,657,758; 4,861,582; and 5,145,664.

DESCRIPTION OF THE INVENTION

One or more objects of the present inventions are accomplished by the provision of a mouthwash composition which is a liquid concentrate comprising (1) about 5–50 weight percent of ethanol; (2) about 5–35 weight percent of water; (3) about 0.5–30 weight percent of a humectant ingredient; (4) about 2–30 weight percent of a suspension of particulate alkali metal bicarbonate ingredient, having an average particle size of about 0.5–5 microns; (5) about 0–3 weight percent of a hydrophilic polymer ingredient; and (6) about 0–5 weight percent of a surfactant ingredient.

In another embodiment this invention provides a method of practicing oral hygiene which involves diluting a liquid mouthwash concentrate as defined above with about 0.2–4 parts by volume of water per part by volume of liquid concentrate, and rinsing the oral cavity with the diluted mouthwash composition.

In another embodiment this invention provides a process for preparing a mouthwash product which comprises (1) forming a liquid medium of constituents comprising (a) about 5–50 parts by weight of ethanol, (b) about 0.5–30 parts by weight of a humectant ingredient, (c) about 0–5 parts by weight of a hydrophilic polymer ingredient, and (d) about 0–5 parts by weight of a surfactant ingredient; and (2) diluting the liquid medium with about 10–35 parts by weight of a 10–30 weight percent aqueous solution of alkali metal bicarbonate; wherein the diluted liquid medium contains a suspension of particulate alkali metal bicarbonate ingredient having an average particle size of about 0.5–5 microns.

The ethanol ingredient normally is employed with a 5 percent content of water. Part or all of the ethanol can be substituted with a nontoxic cosmetic monohydric alcohol which is water-soluble. For example, about 5–80 percent of the ethanol can be substituted with isopropanol.

The humectant ingredient adds body and a pleasant mouthfeel to the liquid mouthwash medium. Suitable humectant compounds include propylene glycol, glycerol, sorbitol, mannitol, corn syrup, β-cyclodextrin, amylodextrin, and the like.

A surfactant can be added as an optional ingredient in a quantity of about 0.2–2 weight percent, and preferably is selected from orally-compatible nonionic and anionic polymers which are commercially available for oral hygiene applications.

Nonionic oral surfactants are illustrated by laurate esters of sorbitol consisting of the monoester condensed with about 15–25 moles of ethylene oxide, such as Tween 20 (ICI Americas). Another suitable type of oral surfactants are the polymers of polyoxyethylene and polyoxypropylene, such as Pluronic F-108 (BASF-Wyandotte).

Anionic oral surfactants are illustrated by alkyl sulfonates and sulfates, such as sodium lauryl sulfate or a sulfonated monoglyceride of a $C_{10}$–$C_{18}$ fatty acid.

A hydrophilic polymer can be added as an optional ingredient in a quantity of about 0.01–2 weight percent to thicken the mouthwash liquid medium, and to stabilize the solid particle phase which is suspended in the liquid medium. The presence of a hydrophilic polymer also enhances mouthfeel, and increases the content of residual mouthwash which adheres to the oral cavity surfaces and extends the beneficial after-effects of the oral cavity rinse.

Suitable hydrophilic polymers include hydrocolloids, cellulose derivatives, polyvinyl derivatives, and the like, such as gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyvinylpyrrolidone, polyethylene glycol, polyacrylamide, gelatin, polyvinyl alcohol, polyvinyl acetate, polyvinyl alcohol/polyvinyl acetate, and the like.

Many of the hydrophilic polymers are large volume commercial products. Sodium carboxymethyl cellulose (CMC) is available in powder or granular form having a particle size of 5–200 microns. CMC is available in a degree of substitution (DS) range of 0.38–1.4.

The term "hydrophilic" as employed herein refers to a water-soluble or water-dispersible organic polymer which has a solubility of at least one gram per 100 grams of water at 25° C.

The alkali metal bicarbonate ingredient is selected from sodium bicarbonate, potassium bicarbonate, and mixtures thereof.

To achieve a stable suspension of solid particle phase in an invention liquid mouthwash composition, it is essential that the size of the suspended particles is less than about 20 microns, and preferably has a particle size distribution below about 5 microns. Particles which are less than about 0.5 micron in size exhibit colloidal properties, and readily form a liquid medium suspension which is dimensionally stable under long term storage conditions. When the particles are below about 0.2 micron in size, visible light scattering is minimized, and a liquid medium containing the particles as a suspended phase has an optically transparent appearance.

In another embodiment the present invention provides a particulate alkali metal bicarbonate ingredient in which the particles are encapsulated within a hydrophilic organic coating. The hydrophilic polymers recited above can be utilized as the particle encapsulating vehicle. Other suitable hydrophilic organic materials include water-soluble starches such as multodextrin and amylodextrin. Water-soluble starches are commercially available under tradenames such as CAPSUL and STARCH 46 (National Starch Company).

The encapsulation of alkali metal bicarbonate particles is illustrated in Example III. The organic coating typically will comprise about 5–30 weight percent of the total encapsulated particle dry weight. Encapsulated particles which have a zeta potential charge can exhibit increased adherence to dental surfaces.

Encapsulated alkali metal bicarbonate particles are lower in density, and more easily form a stable suspension in a mouthwash liquid medium. As a further advantage, the encapsulated particles have a smoother mouthfeel and have an increased ability to adhere to oral cavity surfaces in comparison with uncoated alkali metal bicarbonate particles. The organic coating additionally functions as a sustained release medium with respect to the core matrix alkali metal bicarbonate of particles which adhere to the surfaces of the oral cavity.

The provision of an alkali metal bicarbonate ingredient as a suspension of particles in a liquid medium has several important advantages. In comparison with alkali metal bicarbonate dissolved in the liquid medium, the solid bicarbonate phase is more stable, and can be present in relatively high concentration. Also, the solid bicarbonate phase is less irritating to the oral cavity surfaces than is the same bicarbonate in solution. Also, a longer lasting and more refreshing clean mouthfeel is provided by the solid particle form of alkali metal bicarbonate ingredient.

A present invention mouthwash can contain one or more additional nontoxic orally-compatible ingredients to contribute properties which are desirable in oral hygiene applications.

One optional ingredient is about 0.1–5 weight percent of a bactericide such as zinc oxide, sodium salicylate, sodium benzoate, thymol, hexachlorophene, domiphene bromide, cetylpyridinium chloride, benzethonium chloride, zinc chloride, potassium chloride, gramicidin, 8-hydroxyquinoline, sodium perborate, hydrogen peroxide, and the like. Oil of rosemary exhibits both bactericide and antioxidant properties.

Another optional ingredient is about 0.01–0.2 weight percent of a colorant, such as FDC Red 40, FDC Green 3, FDC Brown mixture, FDC Yellow 5, DC Red 19, DC Red 33, DC Yellow 10, and the like.

Another optional ingredient is about 0.1–5 weight percent of a flavorant, such as oils of spearmint, peppermint, wintergreen, sassafras, clove, sage, eucalyptus, cinnamon, lemon, orange, methyl salicylate, and the like. Sweetening agents also can be included with the flavorants, such as sucrose, lactose, maltose, sorbitol, sodium cyclamate, sodium saccharin, and the like.

Another optional ingredient is about 0.1–2 weight percent of a skin healing agent, such as allantoin (glyoxal diuride).

Another optional ingredient is about 0.1–3 weight percent of an astringent, such as zinc chloride, zinc sulfate, sodium zinc titrate, and the like.

A present invention liquid mouthwash concentrate typically is transparent or translucent in optical clarity. Dilution of a translucent mouthwash concentrate with water can improve the optical clarity to a transparent liquid medium having a slight haze.

The viscosity of an invention liquid mouthwash can be varied between slightly viscous and a soft gel consistency. A high viscosity mouthwash medium exhibits thixotropic properties. The viscosity can be controlled as required for the various dispensing means contemplated.

The following examples are further illustrative of the present invention. The components and specific ingredients are presented as being typical, and various modifications can be derived in view of the foregoing disclosure within the scope of the invention.

EXAMPLE I

This Example illustrates the preparation of ultrafine alkali metal bicarbonate powder by a precipitation method in accordance with the present invention.

A 5 weight percent aqueous solution of sodium bicarbonate is added dropwise to a stirred volume of ice-cooled methanol solvent. The addition is continued until about 20 percent by volume of aqueous solution has been admixed. The resultant monoclinic needles are collected by filtration, and dried under vacuum at 60° C.

The primary acicular particles have a size distribution substantially in the range of 0.2–1 micron, and a surface area of about 10 square meters per gram (BET; ASTM D3663-78).

EXAMPLE II

This Example illustrates the preparation of ultrafine alkali metal bicarbonate powder by a spray-dry method in accordance with the present invention.

An aqueous solution is prepared which contains 3 grams of sodium bicarbonate and 3 grams of potassium bicarbonate per 100 grams of water.

The aqueous solution is sprayed as a fine mist through an inlet nozzle located in the central section of a cylindrical tower which contains air heated at 140° C. The contained column of air has a slow upward flow, at a rate which carries water vapor upward and through an outlet near the top of the tower, and permits the countercurrent settling of crystalline alkali metal bicarbonate particles to a cool collection zone in the bottom of the tower.

The sprayed mist has a droplet size of about 10–15 microns in diameter. The alkali metal bicarbonate particles have a size distribution substantially in the range of about 100–600 nanometers, and a surface area of about 12 square meters per gram (BET).

EXAMPLE III

This Example illustrates a procedure for coating a particulate bicarbonate deodorant compound with a hydrophilic organic polymer in accordance with the present invention.

Guar gum (15 g, Supercol, Aqualon Co.,) is dissolved in 150 ml of 50% aqueous ethanol solvent. Sodium bicarbonate (100 g, 90% of particles in 0.1–5 particles size range) is suspended in the solution medium with stirring.

The solvent medium is removed by evaporation under vacuum. A dry free-flowing powder is obtained. The particles are coated with a guar film which is about 20% of the total dry weight of the coated particles.

The procedure is repeated except that hydroxypropylmethylcellulose (Methocel 60 HG, Dow Chemical Co.) is employed as the hydrophilic polymer coating ingredient.

The procedure is repeated except that multodextrin (Lodex 10; Durkee Foods) is employed as the hydrophilic polymer coating ingredient.

EXAMPLE IV

This Example illustrates the preparation of a concentrated mouthwash formulation in accordance with the present invention.

A formulation is prepared from the following ingredients:

|  | Parts by Weight |
| --- | --- |
| ethanol (5% water) | 40.00 |
| sorbitol (70% in water) | 10.00 |
| glycerol | 5.00 |
| water | 25.00 |
| sodium bicarbonate[1] | 12.00 |
| zinc oxide[2] | 3.00 |
| pluronic F-108[3] | 2.00 |
| cetylpyridium chloride | 0.01 |
| sodium salicylate | 0.20 |
| allantoin | 0.20 |
| sodium saccharin | 0.10 |
| FDC Green 3 (2% solution) | 0.25 |
| peppermint oil | 0.20 |

[1]90% of particles in 0.1–5 particle size range.
[2]5–15 nanometers particle size range.
[3]polyoxypropylene polyoxyethylene condensate; BASF- Wyandotte.

A solution is formed of the ethanol, water and sorbitol ingredients. The Pluronic F-108 is added, followed by sodium bicarbonate and zinc oxide and the other ingredients in the listed order with high speed stirring.

The liquid mouthwash concentrate has a translucent optical clarity. The liquid medium has a clear green color when diluted with two parts of water per one part of liquid concentrate.

The preparation is repeated, except that the sodium bicarbonate particles are encapsulated with a 20% by weight coating of hydroxypropylmethylcellulose as describe in Example III.

EXAMPLE V

This Example illustrates the preparation of a concentrated mouthwash formulation in accordance with the present invention.

A formulation is prepared from the following ingredients:

|  | Parts by Weight |
| --- | --- |
| ethanol (5% water) | 40.00 |
| isopropanol | 15.00 |
| propylene glycol | 5.00 |
| xanthan gum | 0.03 |
| sodium lauryl sulfate | 0.30 |
| zinc oxide (5–15 nanometers particle size) | 3.00 |
| benzthonium chloride | 0.01 |
| sodium saccharin | 0.10 |
| FDC Red 40 (1% solution) | 0.80 |
| 4483T flavorant (Carruba Inc.) | 0.30 |
| 30% by weight aqueous potassium bicarbonate | 40.00 |

A solution is formed of the ethanol, isopropanol and propylene glycol. The xanthan gum is added, followed by the other ingredients in the listed order with high speed stirring. The potassium bicarbonate is added to the liquid mixture as a warm solution (40° C.).

The liquid mouthwash concentrate is a viscous, slightly hazy solution having a colloidal suspension phase of zinc oxide and potassium bicarbonate ingredients.

What is claimed is:

1. A mouthwash composition which is a liquid concentrate consisting essentially of (1) about 5–50 weight percent of ethanol; (2) about 5–35 weight percent of water; (3) about 0.5–30 weight percent of a humectant ingredient; (4) about 2–30 weight percent of a suspension of particulate alkali metal bicarbonate ingredient, having an average particle size of about 0.5–5 microns; (5) about 0.1–5 weight percent of zinc oxide bactericide ingredient in the form of a colloidal suspension; (6) about 0–3 weight percent of a hydrophilic polymer ingredient; and (7) about 0–5 weight percent of a surfactant ingredient; wherein said particulate bicarbonate suspension provides a higher content and more stability than bicarbonate dissolved in the liquid medium; and said hydrophilic polymer thickens the mouthwash liquid concentrate medium, stabilizes the particulate bicarbonate suspension phase, enhances mouthfeel, and increases residual mouthwash adherence to oral cavity surfaces; and said liquid mouthwash concentrate has a viscosity varying between slightly viscous and soft gel consistency, and at high viscosity exhibits thixotropic properties; and said liquid mouthwash concentrate has a transparent or translucent optical clarity.

2. A method of practicing oral hygiene which comprises diluting a claim 1 liquid concentrate composition with about 0.2–4 parts by volume of water per part by volume of liquid concentrate, and rinsing the oral cavity with the diluted mouthwash composition.

* * * * *